United States Patent
Bourane et al.

(10) Patent No.: US 9,187,703 B2
(45) Date of Patent: Nov. 17, 2015

(54) CATALYTIC REFORMING SYSTEM FOR PRODUCING REDUCED BENZENE GASOLINE

(71) Applicant: Saudi Arabian Oil Company, Dhahran (SA)

(72) Inventors: Abdennour Bourane, Ras Tanura (SA); Omer Refa Koseoglu, Dhahran (SA)

(73) Assignee: Saudia Arabian Oil Company, Dhahran (SA)

( * ) Notice: Subject to any disclaimer, the term of this patent is extended or adjusted under 35 U.S.C. 154(b) by 0 days.

(21) Appl. No.: 14/330,906

(22) Filed: Jul. 14, 2014

(65) Prior Publication Data

US 2014/0322092 A1 Oct. 30, 2014

Related U.S. Application Data

(62) Division of application No. 13/546,265, filed on Jul. 11, 2012, now Pat. No. 8,801,920.

(60) Provisional application No. 61/593,560, filed on Feb. 1, 2012.

(51) Int. Cl.
| | |
|---|---|
| *C10G 69/08* | (2006.01) |
| *C07C 13/18* | (2006.01) |
| *C10G 35/04* | (2006.01) |
| *C10G 45/44* | (2006.01) |
| *C10G 63/02* | (2006.01) |
| *C01B 3/26* | (2006.01) |
| *C07C 5/10* | (2006.01) |

(52) U.S. Cl.
CPC . *C10G 69/08* (2013.01); *C01B 3/26* (2013.01); *C07C 5/10* (2013.01); *C07C 13/18* (2013.01); *C10G 35/04* (2013.01); *C10G 45/44* (2013.01); *C10G 63/02* (2013.01); *C01B 2203/0277* (2013.01); *C01B 2203/1047* (2013.01); *C01B 2203/1235* (2013.01); *C01B 2203/1258* (2013.01); *C07C 2101/14* (2013.01); *C07C 2521/04* (2013.01); *C07C 2523/42* (2013.01)

(58) Field of Classification Search
CPC ................................................. C10G 69/08
USPC ....................................................... 422/187
See application file for complete search history.

(56) References Cited

U.S. PATENT DOCUMENTS 3,625,879 A * 12/1971 Horne et al. .................. 585/251
5,837,639 A * 11/1998 Kresge et al. ................... 502/64
(Continued)

OTHER PUBLICATIONS

International Search Report and Written Opinion mailed Sep. 20, 2012 in counterpart International Application PCT/US2012/046150.

*Primary Examiner* — Randy Boyer
*Assistant Examiner* — Juan Valencia
(74) *Attorney, Agent, or Firm* — Abelman, Frayne & Schwab; Thomas E. Spath

(57) ABSTRACT

A catalytic reforming process for producing gasoline of reduced benzene content includes the steps of reforming a reformer feedstock that includes a naphtha stream to produce a gasoline reformate product stream; splitting the gasoline reformate product stream into one or more relatively benzene-rich fractions and one or more relatively benzene-lean fractions; and hydrogenating the one or more relatively benzene-rich fractions to produce a cyclohexane-rich effluent, at least a portion of which cyclohexane-rich effluent is recycled to constitute a portion of the reformer feedstock.

7 Claims, 4 Drawing Sheets

(56) References Cited

U.S. PATENT DOCUMENTS

| | | |
|---|---|---|
| 2007/0299294 A1 | 12/2007 | Lin et al. |
| 2010/0063334 A1 | 3/2010 | Vichailak et al. |
| 2013/0006027 A1* | 1/2013 | Yanagawa et al. ............ 585/251 |
| 2013/0184506 A1* | 7/2013 | Yanagawa et al. ............ 585/256 |

* cited by examiner

CATALYTIC REFORMING SYSTEM FOR PRODUCING REDUCED BENZENE GASOLINE

RELATED APPLICATION

This application claims the benefit of U.S. Provisional Patent Application No. 61/593,506 filed Feb. 1, 2012, and U.S. Ser. No. 13/546,265 filed Jul. 11, 2012, the disclosures of which are hereby incorporated by reference.

BACKGROUND OF THE INVENTION

1. Field of the Invention

This invention relates to catalytic reforming apparatus and processes, particularly for producing gasoline of reduced benzene content.

2. Description of Related Art

Refinery products used for fuels are receiving increasing levels of attention. Product specifications are being scrutinized by governmental agencies whose interests are decreased emissions from mobile and stationary sources, and by the industries that produce the engines and vehicles that utilize these fuels.

Regional and national regulations have been in place and continue to evolve concerning gasoline specifications, and automakers have proposed a set of limitations for gasoline and diesel to allow them to manufacture vehicles which will produce significantly lower emissions over their lifetime. Maximum sulfur, aromatics, and benzene levels of 10 parts per million by weight (ppmw), 25 volume % (V %), and 1 V % or less, respectively, have been targeted as goals by regulators. There are cost-effective technology options available to refiners that are offered by several commercial licensors to produce fuels meeting the specifications set for the gasoline pool.

Historically, lead was commonly added to gasoline to increase octane. When the use of lead was phased out due to environmental concerns, no direct substitute existed, and refiners instead have converted certain hydrocarbon molecules used in gasoline blending in order to achieve higher octane ratings. Catalytic reforming, which involves a variety of reactions in the presence of one or more catalysts in the presence of recycle and make-up hydrogen, is a widely used process for refining hydrocarbon mixtures to increase the yield of higher octane gasoline.

Although benzene yields can be as high as 30 V % in reformates, no more than 1 V % can be present in typical gasoline pools. There currently exist methods to remove benzene from reformate, including separation processes and hydrogenation reaction processes. In separation processes, benzene is typically extracted with a solvent and then separated from the solvent in a membrane separation unit or other suitable unit operation. In hydrogenation reaction processes, the reformate is divided into fractions to concentrate the benzene and one or more benzene-rich fractions are hydrogenated.

In a typical refinery, naphtha is reformed after hydrodesulfurization to increase the octane number of the gasoline. The reformate contains a high level of benzene which must be reduced in order to meet requisite fuel specifications that are commonly in the range of from about 1-3 V % benzene, with certain geographic regions targeting a benzene content of less than 1 V %. Benzene hydrogenation is a well-established process that can be used to reduce the benzene content of the reformate product stream.

A flow diagram including a prior art catalytic reforming process and apparatus 100 is shown in FIG. 1. A reforming unit 120 is integrated with a benzene saturation unit 130 for the processing of a hydrocarbon fraction to produce gasoline and light reformate. A naphtha stream 101 is first hydrotreated in hydrotreating unit 110 to produce a hydrotreated naphtha stream 102. Hydrotreating unit 110 operates under conditions of, e.g., temperature, pressure, hydrogen partial pressure, liquid hourly space velocity (LHSV), catalyst selection/loading that are effective to remove at least enough sulfur and nitrogen to meet requisite product specifications. For instance, hydrotreating in conventional naphtha reforming systems generally occurs under relatively mild conditions that are effective to remove sulfur and nitrogen to less than 0.5 ppmw levels.

The hydrotreated naphtha stream 102 is reformed in reforming unit 120 to produce a gasoline reformate product stream 103. In general, the operating conditions for reforming unit 120 include a temperature in the range of from 260° C. to 560° C., and in certain embodiments from 450° C. to 560° C.; a pressure in the range of from 1 bar to 50 bars, and in certain embodiments from 1 bar to 20 bars; and a LHSV in the range of from $0.5\ h^{-1}$ to $40\ h^{-1}$, and in certain embodiments from $0.5\ h^{-1}$ to $2\ h^{-1}$.

The total reformate stream 103 is passed to a reformate splitter 125 and separated into one or more relatively benzene-rich fractions 107 and one or more relatively benzene-lean fractions 104 and 106. Typically, a relatively benzene-rich middle fraction 107 comprises about 10-20 V % of the total reformate and contains about 20-30 V % benzene. In contrast, the relatively benzene-lean heavy reformate bottom fraction 106 comprises about 40-80 V % of the total reformate and has a benzene content generally in the range of from about 0.3-1 V %, which is sufficiently low to be passed to a gasoline pool 135 without further processing. The light reformate top fraction 104 which includes about 10-25 V % of the total reformate, contains about 5-30 V % benzene and is recovered or blended with other product pools.

The middle fraction 107, or "heart cut," which contains a majority of the benzene content of reformate 103, is passed to a hydrogenation unit 130, which is also referred to as a benzene saturation unit, with a predetermined amount of hydrogen gas 105 for conversion reactions including conversion of benzene to cyclohexane and for the production of a benzene-lean and in certain embodiments an essentially benzene-free, gasoline blending component 108. The benzene saturation unit 130 typically contains an effective quantity of catalyst having a suitable level of active materials possessing hydrogenation functionality, such as nickel, platinum or other Group VIIIB metals, supported on an alumina substrate.

In general, the operating conditions for hydrogenation unit 130 include a temperature in the range of from 35° C. to 200° C., in certain embodiments from 95° C. to 140° C.; a pressure in the range of from 5 bars to 50 bars, in certain embodiments from 5 bars to 25 bars; and a LHSV in the range of from $0.5\ h^{-1}$ to $10\ h^{-1}$, in certain embodiments from $1\ h^{-1}$ to $4\ h^{-1}$.

The benzene-lean blending component 108 is mixed with the remaining gasoline pool constituents including the benzene-lean heavy reformate bottom fraction 106. For instance, when blended with the heavy reformate fraction 104 which can contain up to 1 V % benzene, a final gasoline product can be recovered which contains less than about 1 V % benzene.

A typical gasoline blending pool includes $C_4$ and heavier hydrocarbons having boiling points of less than about 205° C. In the catalytic reforming process, paraffins and naphthenes are restructured to produce isomerized paraffins and aromatics of relatively higher octane numbers. The catalytic reforming converts low octane n-paraffins to i-paraffins and naphthenes. Naphthenes are converted to higher octane aromatics. The aromatics are left essentially unchanged or some may be hydrogenated to form naphthenes due to reverse reactions taking place in the presence of hydrogen.

The reactions involved in catalytic reforming are commonly grouped into the four categories of cracking, dehydrocyclization, dehydrogenation and isomerization. A particular hydrocarbon/naphtha feed molecule may undergo more than one category of reaction and/or may form more than one product.

Catalytic reforming processes are catalyzed by either mono-functional or bi-functional reforming catalyst which contains precious metals, i.e., Group VIIIB metals, as active components. A bi-functional catalyst has both metal sites and acidic sites. Refineries generally use a platinum catalyst or platinum alloy supported on alumina as the reforming catalyst.

The hydrocarbon/naphtha feed composition, the impurities present therein, and the desired products will determine such process parameters as choice of catalyst(s), process type, and the like. Types of chemical reactions can be targeted by a selection of catalyst or operating conditions known to those of ordinary skill in the art to influence both the yield and selectivity of conversion of paraffinic and naphthenic hydrocarbon precursors to particular aromatic hydrocarbon structures.

Referring to FIG. 2, a prior art process flow of an embodiment of a catalytic reforming system 200 is illustrated. Catalytic reforming processes typically include a series of reactors 260A, 260B, 260C and 260D which operate at temperatures of about 480° C. A feedstock 251 is introduced into a heat exchanger 250 to increase its temperature. The heated feedstock 252 is treated in the reforming reactors to produce a hot product hydrogen and reformate stream 261.

The reforming reactions are endothermic resulting in the cooling of reactants and products, requiring heating of effluent, typically by direct-fired furnaces 255A, 255B, 255C and 255D, prior to charging as feed to a subsequent reforming reactor. As a result of the very high reaction temperatures, catalyst particles are deactivated by the formation of coke on the catalyst which reduces the available surface area and active sites for contacting the reactants.

Hot product hydrogen and reformate stream 261 passes through heat exchanger 250 and then to separator 270 for recovery of hydrogen stream 271 and a separator bottoms stream 273. Recovered hydrogen stream 271 is split and a portion of the hydrogen 272 is fed to compressor 290 and recycled back to the reformer reactors with hydrogen stream 251. The remaining portion 274 of the hydrogen gas is sent to other refining unit operations, such as hydrotreating. The separator bottoms stream 273 is sent to a stabilizer column 280 to produce a light end stream 281 and a reformate stream 282.

There are several types of catalytic reforming process configurations which differ in the manner in which they regenerate the reforming catalyst to remove the coke formed in the reactors. Catalyst regeneration, which involves combusting the detrimental coke in the presence of oxygen, includes a semi-regenerative process, cyclic regeneration and continuous regeneration. Semi-regeneration is the simplest configuration, and the entire unit, including all reactors in the series is shutdown for catalyst regeneration in all reactors. Cyclic configurations utilize an additional "swing" reactor to permit one reactor at a time to be taken off-line for regeneration while the others remain in service. Continuous catalyst regeneration configurations, which are the most complex, provide for essentially uninterrupted operation by catalyst removal, regeneration and replacement. While continuous catalyst regeneration configurations include the ability to increase the severity of the operating conditions due to higher catalyst activity, the associated capital investment is necessarily higher.

The problem faced by refineries is how to most economically reduce the benzene content in the reformate products sent to the gasoline pool by modifying the processes and apparatus of existing systems practicing the prior art processes described above.

SUMMARY OF THE INVENTION

In accordance with the process and system of the present invention, a portion of the reformate from the reformer unit is hydrogenated to reduce the benzene content of the gasoline. A portion of the cyclohexane and its alkyl derivatives produced in the hydrogenation unit are recycled to the reformer unit. This results in the reformer unit feed having a higher concentration of cyclohexane and its alkyl derivatives that readily release hydrogen and thereby increase the available hydrogen content and the relative hydrogen purity. Only relatively minor changes are required to the apparatus and control elements of the prior art reformer systems described above.

BRIEF DESCRIPTION OF THE DRAWINGS

The invention will be described in further detail below and with reference to the attached drawings in which the same or similar elements are referred to by the same numerals, and where.

DETAILED DESCRIPTION OF THE INVENTION

Figure 3:
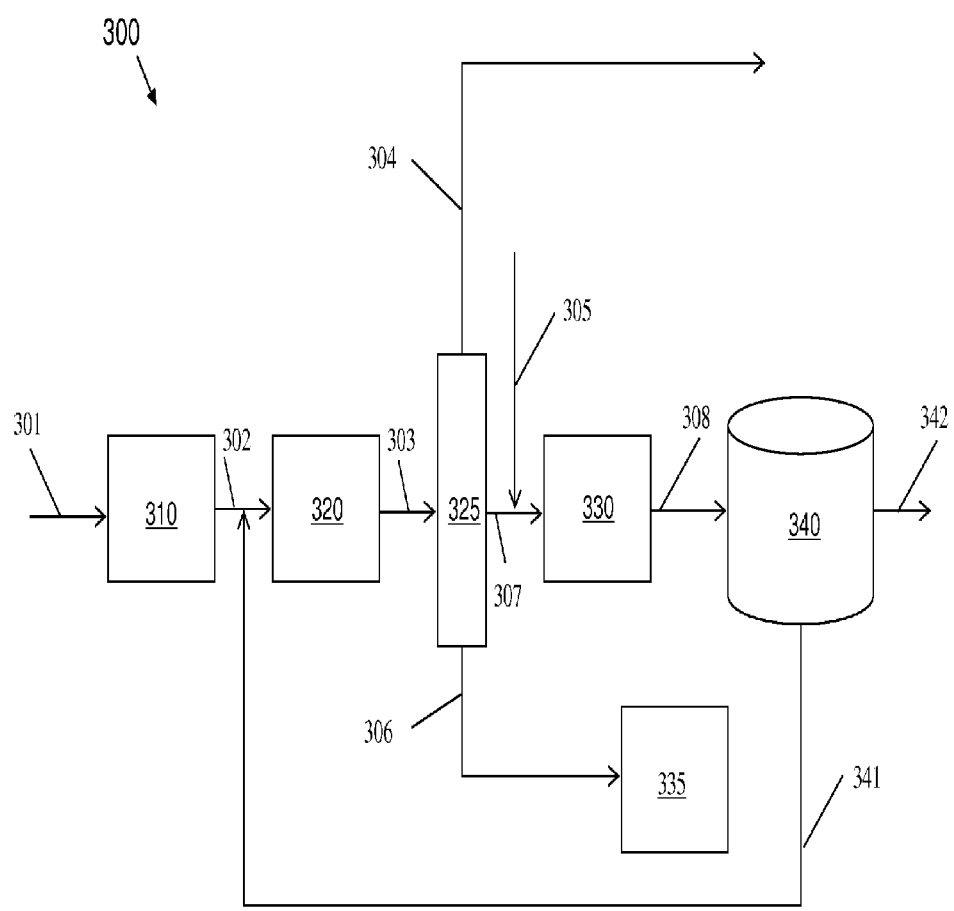
FIG. 3 is a process flow diagram illustrating an embodiment of the present invention.

Referring now to the process diagram of FIG. 3, an integrated system 300 in accordance with the present invention provides for improved gasoline production by increasing the hydrogen available for reaction during catalytic reforming. As will be described in more detail below, the process includes catalytic reforming and recycle of the benzene saturation unit effluent. The system and process of the invention can be implemented as a cost-saving upgrade to enhance the quality of the reformate gasoline product and reduce the overall environmental impact of the product. The integrated system includes a reforming unit 320 and a benzene saturation unit 330 in which a portion of the benzene saturation unit effluent is recycled to the reforming unit.

A naphtha stream 301 is hydrotreated in hydrotreating unit 310 to produce a hydrotreated naphtha stream 302, which is reformed in a reforming unit 320 to produce a gasoline reformate product stream 303. The reformate stream 303 is separated in a reformate splitter 325 into one or more relatively benzene-rich fractions 307 and one or more relatively benzene-lean fractions 304 and 306. Stream 304 is recovered or blended with other products, and stream 306 is passed to a gasoline pool 335 without further processing. The middle fraction 307, or "heart cut," which contains a majority of the benzene content of reformate 303, is passed to a hydrogenation or benzene saturation unit 330, along with a hydrogen stream 305 for conversion reactions including conversion of benzene to cyclohexane and for the production of a benzene-lean, and in certain embodiments an essentially benzene-free, hydrogenated reformate 308. The benzene saturation unit typically contains an effective quantity of catalyst having a suitable level of active materials possessing hydrogenation functionality, such as nickel or platinum.

Hydrogenated reformate 308 is passed to a surge drum 340 and at least a portion 341 of hydrogenated reformate is recycled to the process upstream of the reforming unit 320 where it is combined with the hydrotreated naphtha stream 302. The remaining portion 342 of hydrogenated reformate is mixed with the remaining gasoline pool constituents including the heavy fraction 306.

Recycling of the benzene-lean middle reformate fraction 341 which contains a relatively high concentration of cyclohexane and its alkyl derivatives increases the hydrogen purity of the feed to the catalytic reformer. The recycle stream 341 is referred to herein as the "cyclohexane-rich effluent". In addition, the benzene content of the product stream will be significantly reduced or eliminated. Since this recycle stream 341 is an internal stream, there will be no decrease in product yields. The rate of recycle can be in the range of from about 2-60 V % of the reformer feedstock.

Figure 1:
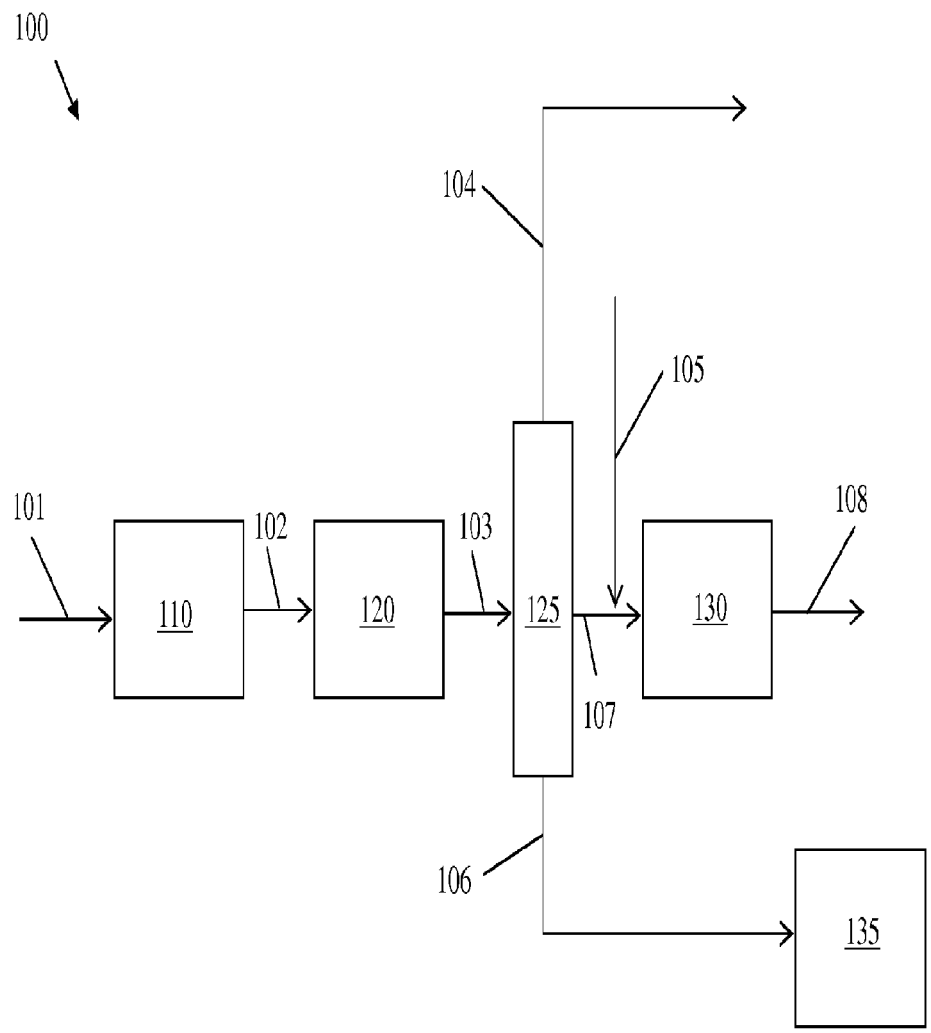
FIG. 1 is a schematic diagram of a prior art catalytic reforming process.
Figure 2:
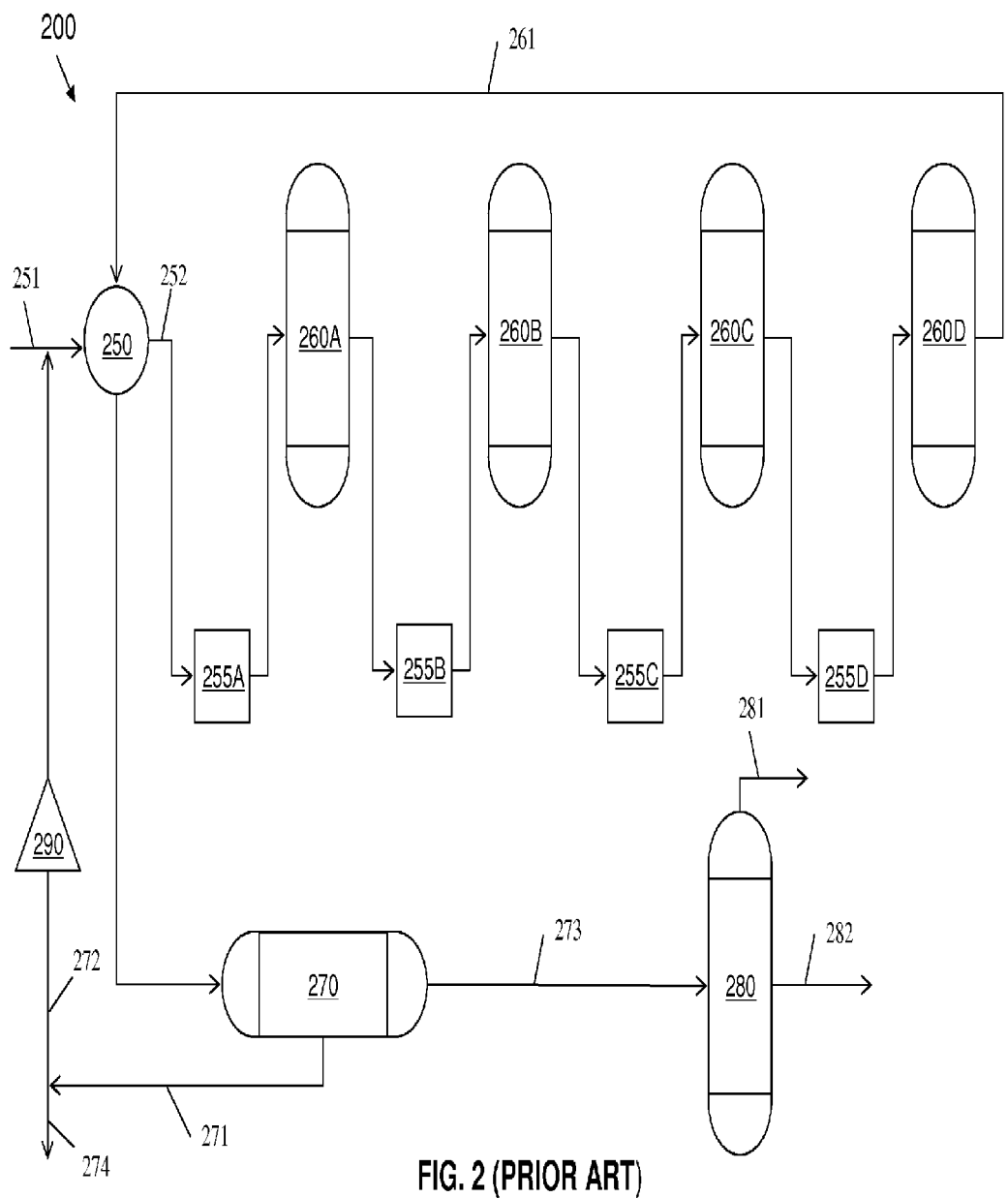
FIG. 2 is a process flow diagram of a reformer system in accordance with the prior art.

Reforming unit 320 can be, for example, a prior art system similar to that shown in FIG. 2, or any other unit operation or series of unit operations known to function as a reforming unit, including those briefly described above, e.g., semi-regenerative configurations, cyclic configurations and continuous catalyst regeneration configurations.

In certain embodiments, the cyclohexane-rich effluent can be used as a hydrogen carrier, for instance in fluid communication with other processes in the refinery limits that can benefit from the hydrogen content of the cyclohexane. In further embodiments, the liquid cyclohexane-rich effluent can be conveyed by other means, e.g., container, tanker or pipeline, to remote locations where it is impractical to obtain hydrogen from other sources.

The hydrogen stream 305 can be derived from any hydrogen purge streams available in the refinery. For instance, all or a portion of the hydrogen stream 305 can be derived from a purge stream having a pressure in the range of from 30 to 150 bars and having a hydrogen concentration in the range of from 20-80 V %.

In accordance with the present process, a portion of the hydrogenation unit product cyclohexane and its alkyl derivatives are recycled to the reformer unit. Accordingly, the reformer feed includes a higher concentration of cyclohexane and its alkyl derivatives that readily release hydrogen and thereby increase the hydrogen content and the relative hydrogen purity of the reformer feed. For example, at 10 V % and 40 V % cyclohexane recycle rates, the absolute hydrogen purity is increased by 1.5 V % and 5 V %, respectively.

An analysis of the process of the invention was conducted using PRO/II steady-state simulation software. Under the conditions of the simulation, a hydrotreated naphtha derived from a blend of Arab light and heavy crudes is reformed in a fixed-bed reforming unit over a platinum catalyst. The reformer product yields are given in Table 1.

TABLE 1

|  |  | MBD (MMSCF) | Kg/D |
|---|---|---|---|
| In |  |  |  |
| Feed | MBD | 29.99 | 3,576,308 |
| Out |  |  |  |
| Reformate | MBD | 24.57 | 2,929,973 |
| H$_2$ Recycle | MMSCF | (129.92) | 686,328 |
| Off Gas | MMSCF | (1.7) | 52,725 |
| LPG | MBD | 0.293 | 17,860 |
| Total Out |  |  | 3,686,885 |
| H$_2$Recycle Purity | V % | 78.908 |  |

The reformate is fractionated into three fractions in a splitter containing 31 trays to produce 12.3 W % of a mid-reformate fraction, of which 15 V % is benzene. Stream flow rates and compositions calculated from the PRO/II simulations are shown in Table 2.

TABLE 2

| Stream Name | Feedstock | Tops | MID | BTMS |
|---|---|---|---|---|
| Stream Description |  |  |  |  |
| Phase | Liquid | Liquid | Liquid | Liquid |
| Temperature, °C. | 93 | 146 | 192 | 259 |
| Total Mass Rate, Kg/h | 1000 | 209.87 | 123.27 | 666.86 |
| Total Weight Comp. Percents |  |  |  |  |
| NC4 | 0.073 | 0.35 | 8.38E−06 | 1.12E−09 |
| IC5 | 4.15 | 19.76 | 0.019 | 6.15E−06 |
| NC5 | 2.96 | 14.09 | 0.03 | 1.28E−05 |
| CP | 0.14 | 0.66 | 0.009 | 1.82E−05 |
| 2MP | 4.07 | 17.92 | 2.54 | 0.001 |
| NC6 | 3.62 | 12.24 | 8.48 | 0.005 |
| MCP | 0.17 | 0.40 | 0.65 | 0.0017 |
| BENZENE | 4.27 | 11.07 | 15.00 | 0.14 |
| NC7 | 1.76 | 0.03 | 9.97 | 0.79 |
| MCH | 0.016 | 2.80E−05 | 0.02 | 0.02 |
| TOLUENE | 16.07 | 0.005 | 7.88 | 22.64 |
| 23MP | 0.90 | 0.069 | 6.29 | 0.17 |
| 22MB | 1.02 | 4.78 | 0.15 | 8.53E−05 |
| 23MB | 0.90 | 3.95 | 0.58 | 0.0004 |
| 3MP | 3.09 | 12.40 | 3.95 | 0.0024 |
| 22MP | 0.37 | 0.25 | 2.57 | 0.0060 |
| 24MP | 0.39 | 0.23 | 2.72 | 0.006 |
| 223B | 0.06 | 0.02 | 0.41 | 0.003 |
| 33MP | 0.33 | 0.045 | 2.37 | 0.043 |
| 2MHX | 2.05 | 0.20 | 15.23 | 0.20 |
| 3MHX | 2.52 | 0.15 | 17.75 | 0.45 |
| 3EPN | 0.27 | 0.009 | 1.69 | 0.09 |
| 22HX | 0.06 | 4.04E−05 | 0.11 | 0.07 |
| 25HX | 0.06 | 2.30E−05 | 0.09 | 0.08 |
| 24HX | 0.11 | 2.63E−05 | 0.12 | 0.14 |
| 33HX | 0.05 | 2.30E−06 | 0.02 | 0.06 |
| 23HX | 0.07 | 1.30E−06 | 0.02 | 0.11 |

TABLE 2-continued

| Stream Name | Feedstock | Tops | MID | BTMS |
|---|---|---|---|---|
| 2MHP | 0.23 | 3.48E−06 | 0.07 | 0.34 |
| 4MHP | 0.18 | 2.01E−06 | 0.04 | 0.26 |
| 34HX | 0.05 | 3.18E−07 | 0.007 | 0.07 |
| 3MHP | 0.28 | 1.78E−06 | 0.05 | 0.41 |
| OCTANE | 0.23 | 1.62E−07 | 0.01 | 0.34 |
| NONANE | 0.02 | 1.73E−12 | 1.59E−05 | 0.02 |
| DECANE | 0.09 | 1.73E−15 | 2.15E−06 | 0.14 |
| NC12 | 0.09 | 4.80E−22 | 3.23E−09 | 0.14 |
| NC13 | 0.1 | 0 | 1.18E−10 | 0.15 |
| EBENZENE | 4.36 | 1.56E−07 | 0.03 | 6.53 |
| OXYLENE | 5.59 | 2.61E−08 | 0.017 | 8.38 |
| MXYLENE | 4.01 | 5.90E−08 | 0.02 | 6.02 |
| PXYLENE | 8.93 | 1.49E−07 | 0.05 | 13.38 |
| PRBENZEN | 1.07 | 1.85E−11 | 0.0003 | 1.60 |
| 1C3M | 0.06 | 0.004 | 0.36 | 0.02 |
| ECP | 0.02 | 1.77E−05 | 0.02 | 0.02 |
| CTCP | 0.07 | 2.07E−07 | 0.005 | 0.10 |
| 1HEXENE | 0.03 | 0.11 | 0.03 | 1.84E−05 |
| T2PENTEN | 0.04 | 0.17 | 0.0004 | 2.01E−07 |
| C2PENTEN | 0.02 | 0.09 | 0.0002 | 1.19E−07 |
| 2M2BUTEN | 0.11 | 0.50 | 0.001 | 5.16E−07 |
| 3M1PNTEN | 0.05 | 0.24 | 0.01 | 7.77E−06 |
| C2HEXENE | 0.03 | 0.08 | 0.08 | 6.61E−05 |
| 1HEPTENE | 0.05 | 0.002 | 0.32 | 0.01 |
| HEPTENE2 | 0.04 | 0.0003 | 0.17 | 0.03 |
| TBBENZEN | 5.73 | 2.82E−12 | 0.0003 | 8.60 |
| SBBENZEN | 0.08 | 9.69E−15 | 2.63E−06 | 0.12 |
| BBENZENE | 0.75 | 3.33E−15 | 6.20E−06 | 1.12 |
| 123MBENZ | 1.27 | 2.78E−13 | 5.06E−05 | 1.90 |
| 2EMXYL | 0.44 | 3.36E−16 | 1.60E−06 | 0.66 |
| 2EPXYL | 0.49 | 6.77E−16 | 2.42E−06 | 0.73 |
| 12DM3EBZ | 0.18 | 3.04E−17 | 3.34E−07 | 0.28 |
| 4EOXYL | 0.84 | 4.73E−16 | 2.77E−06 | 1.26 |
| TMBZ | 0.46 | 3.00E−17 | 5.68E−07 | 0.68 |
| 1234TMBZ | 0.63 | 4.94E−18 | 2.78E−07 | 0.94 |
| 5EMXYL | 0.05 | 1.26E−16 | 3.24E−07 | 0.07 |
| 13DEBZ | 0.32 | 2.80E−15 | 3.46E−06 | 0.48 |
| 1M3PRBZ | 0.87 | 5.34E−15 | 8.66E−06 | 1.30 |
| 1M2PRBZ | 0.32 | 1.00E−15 | 2.26E−06 | 0.49 |
| 1M4PRBZ | 0.16 | 6.02E−16 | 1.27E−06 | 0.24 |
| 2M1PNTEN | 0.05 | 0.20 | 0.07 | 5.18E−05 |
| M3EZ | 3.91 | 1.73E−11 | 0.0007 | 5.86 |
| M4EZ | 1.77 | 1.44E−11 | 0.0003 | 2.66 |
| 124MBENZ | 1.55 | 1.42E−12 | 0.0001 | 2.33 |
| M2EZ | 1.68 | 3.43E−12 | 0.0002 | 2.53 |
| NAPHTHLN | 0.30 | 2.42E−18 | 9.93E−08 | 0.45 |
| INDANE | 0.18 | 9.71E−14 | 9.32E−06 | 0.27 |
| MDIPBN | 0.33 | 9.74E−19 | 1.14E−07 | 0.50 |
| PDIPBN | 0.03 | 8.76E−21 | 3.88E−09 | 0.05 |
| PNBENZEN | 2.35 | 3.09E−18 | 5.59E−07 | 3.52 |

The mid-reformate fraction is sent to the benzene saturation unit for full saturation over a platinum catalyst at a pressure of 15 bars, a temperature of 100° C. and a LHSV of 1 h$^{-1}$. The hydrogenated benzene fraction, i.e., cyclohexane, is recycled back to the reformer unit at various rates that are indicated in Table 3.

TABLE 3

| | | Recycle Rate | | | | | |
|---|---|---|---|---|---|---|---|
| | | 1.845 | 10 | 20 | 30 | 40 | 50 |
| Benzene | Moles | 693,051 | 3,756,375 | 7,512,750 | 11,269,125 | 15,025,500 | 18,781,875 |
| Benzene | Kg | 54,058 | 292,997 | 585,995 | 878,992 | 1,171,989 | 1,464,986 |
| Hydrogen | Moles | 2,079,154 | 11,269,125 | 22,538,250 | 33,807,375 | 45,076,500 | 56,345,625 |
| Hydrogen | Kg | 4,192 | 22,719 | 45,437 | 68,156 | 90,874 | 113,593 |
| Hydrogen | Liter | 49,257,227 | 266,976,840 | 533,953,681 | 800,930,521 | 1,067,907,362 | 1,334,884,202 |
| Hydrogen | MMSCF | 1.74 | 9.43 | 18.86 | 28.29 | 37.72 | 47.14 |
| Hydrogen* | % | 1.7 | 9.2 | 18.4 | 27.6 | 36.8 | 46.0 |
| Hydrogen Purity | | 79.21 | 80.47 | 81.84 | 83.04 | 84.12 | 85.08 |
| Change in purity | | 0.30 | 1.56 | 2.93 | 4.14 | 5.21 | 6.17 |

*Additional hydrogen make-up

Figure 4:
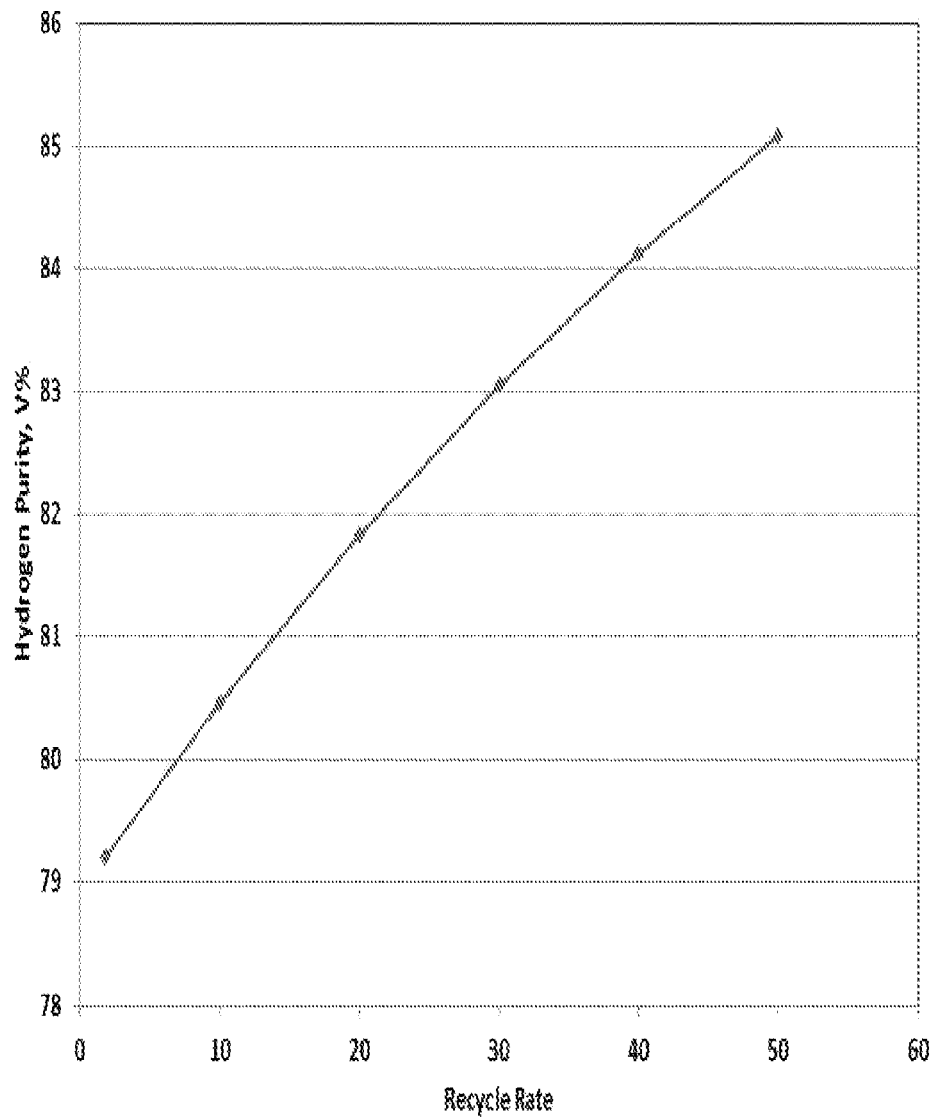
FIG. 4 is a graphic illustration showing the hydrogen production rate increase that results from increasing the recycle rate in accordance with the present invention.

The results are graphically illustrated in FIG. 4 where the hydrogen production rate increases with an increase in the recycle rate, at a rate of 0.9 V % per V % of recycle. Similarly, hydrogen purity increases at a rate of 0.12 V % per V % of recycle.

The method and system of the present invention have been described above and in the attached drawings and modifications will be apparent to those of ordinary skill in the art and the scope of protection for the invention is to be determined by the claims that follow.

The invention claimed is:

1. An integrated catalytic reforming system comprising:
   a reforming unit including an inlet in fluid communication with a conduit for receiving a hydrotreated naphtha stream and a recycle conduit, the reformer also including an outlet for discharging a gasoline reformate product stream;
   a fractionation unit reformate splitter including an inlet in direct fluid communication with the outlet of the reforming unit, one or more relatively benzene-rich fraction outlets and one or more relatively benzene-lean fraction outlets;
   a hydrogenation unit including a hydrogen inlet, a benzene-rich fraction inlet and a cyclohexane-rich product outlet, the benzene-rich fraction inlet being in direct fluid communication with at least one of the fractionation unit reformate splitter benzene-rich fraction outlets; and
   the recycle conduit being in fluid communication with the hydrogenation unit cyclohexane-rich product outlet and the reforming unit inlet for recycling at least a portion of the cyclohexane-rich product to the reforming unit.

2. The system of claim 1 including a surge drum and in which a surge drum inlet is in fluid communication with the cyclohexane-rich product outlet of the hydrogenation unit and a surge drum outlet is in fluid communication with the reforming unit inlet.

3. The system of claim 2 in which the surge drum also includes an outlet for passing a portion of the cyclohexane-rich product to a gasoline pool holding vessel.

4. The system of claim 1 in which the hydrogenation unit contains a catalyst with hydrogenation functionality.

5. The system of claim 4, wherein the catalyst includes active metals selected from Group VIIIB of the Periodic Table.

6. The system of claim 4, wherein the catalyst is supported on alumina.

7. The system of claim 5, wherein the hydrogenation catalyst contains nickel or platinum.

\* \* \* \* \*